United States Patent [19]

Slinkard et al.

[11] 4,168,391

[45] Sep. 18, 1979

[54] PRODUCTION OF ETHANOL FROM METHANOL

[75] Inventors: William E. Slinkard, Corpus Christi, Tex.; Anthony B. Baylis, Berkeley Heights, N.J.

[73] Assignee: Celanese Corporation, New York, N.Y.

[21] Appl. No.: 857,631

[22] Filed: Dec. 5, 1977

[51] Int. Cl.$^2$ .............................................. C07C 29/00
[52] U.S. Cl. .................................................... 568/902
[58] Field of Search .................... 260/642 B; 568/902

[56] References Cited

U.S. PATENT DOCUMENTS

| 2,623,906 | 12/1952 | Gresham | 260/642 B |
| 3,940,432 | 2/1976 | Walker et al. | 260/449 L |

*Primary Examiner*—Joseph E. Evans
*Attorney, Agent, or Firm*—Stewart N. Rice; Ralph M. Pritchett

[57] ABSTRACT

An improvement in the process wherein carbon monoxide and hydrogen are reacted in the liquid phase in the presence of a cobalt carbonyl catalyst whereby increased amounts of ethanol may be produced, which improvement comprises conducting the reaction in the presence of a non-polar, substantially inert, oxygenated hydrocarbon solvent.

3 Claims, No Drawings

PRODUCTION OF ETHANOL FROM METHANOL

BACKGROUND OF THE INVENTION

The liquid phase reaction of methanol with synthesis gas (a mixture of hydrogen and carbon monoxide) in the presence of a cobalt carbonyl catalyst is well known; for example, see U.S. Pat. No. 2,457,204 issued Dec. 28, 1948 to Richard E. Brooks, and I. Wender et al., Science, Vol. 113, p. 206–207 (1951). A variety of products are produced in the reaction including methyl acetate, acetaldehyde, dimethylacetal (also known as 1,1-dimethoxy ethane), ethanol, propanol, isopropanol, butanol, isobutanol, ethyl acetate, methane, water and other compounds. That a wide variety is produced is one disadvantage of the reaction and research has been directed toward making the reaction more selective in the production of a particular desired product.

Much of the prior research has been directed toward increasing production of methyl acetate, and research toward increase in ethanol selectivity has been largely neglected. For example, see U.S. Pat. No. 2,727,902 issued Dec. 20, 1955 to Reppe et al, and U.S. Pat. No. 2,805,248 issued Sept. 3, 1957 to Friederich et al, both of which deal mainly with the production of acids and esters. Since ethanol is an important commercial product, more efficient means for its productions is desirable.

It is thus an object of the present invention to provide a new and useful process for production of ethanol. It is a particular object of the present invention to provide a new and useful process for production of ethanol by the reaction of methanol with synthesis gas. It is a still further object of the present invention to improve the process wherein methanol and synthesis gas are reacted in the presence of a cobalt carbonyl catalyst such that there is an increased selectivity in the production of ethanol. Additional objects will become apparent from the following description of the present invention.

SUMMARY

The foregoing and additional objects are accomplished by the present invention which in one of its aspects is an improvement in a liquid phase reaction process wherein methanol in the liquid phase is reacted, at elevated temperatures and superatmospheric pressures and in the presence of a catalyst consisting of cobalt carbonyl, with a gas comprised of carbon monoxide and hydrogen to produce a product comprising ethanol, which improvement comprises conducting the reaction in a liquid solvent in which the methanol and cobalt carbonyl catalyst are soluble under reaction conditions; said solvent having a dielectric constant less than that of methanol such that it is relatively non-polar, and being one which does not strongly coordinate with said cobalt carbonyl; said solvent being an oxygenated hydrocarbon free of carboxyl and aldehyde groups, the only oxygen atoms present in said oxygenated hydrocarbon being present as etheral oxygen, oxygen of a hydroxyl group, oxygen of an ester group or oxygen of a ketone carbonyl group of a ketone; said solvent being one which will be liquid under the reaction conditions and which has a boiling point at atmospheric pressure of at least 65° C. and which is a liquid at 35° C. and atmospheric pressure; said solvent being substantially inert under the reaction conditions such that it does not react to any appreciable extent with itself or with the catalyst, or with the reactants and reaction products present in the reaction mixture; and, said solvent being free of ethylenic and acetylenic unsaturation.

DETAILED DESCRIPTION OF THE INVENTION

The novelty of the present invention resides in the use of a particular type of solvent medium for the reaction. Use of the solvent unexpectedly results in an increased selectivity to ethanol, and the combined selectivity of products such as methyl acetate, acetaldehyde and dimethylacetal is reduced. There has been some disclosure in the prior art that solvents may be used in the reaction of methanol and synthesis gas in the presence of a cobalt-containing catalyst. For example, see U.S. Pat. No. 2,727,902 at Column 3, Lines 10–17, and U.S. Pat. No. 2,805,248 at Column 3, Lines 47–52. The cobalt-containing catalysts disclosed in these references are not cobalt carbonyl catalysts even though cobalt carbonyl may have been used in the synthesizing of the catalysts. It may be also seen from these references that they were mainly for production of oxygenated products other than ethanol. The catalyst utilized in the present invention is one which consists of cobalt carbonyl, that is, it is unmodified by the addition of other components.

The solvent which may be used in the invention must meet several criteria in order to be satisfactory. The solvent must be an oxygenated hydrocarbon. By "oxygenated hydrocarbon" is meant one which is composed only of carbon, hydrogen and oxygen. Further, the oxygenated hydrocarbon must be one which is free of carboxyl (—COOH) and aldehyde (—CHO) groups, and one wherein the only oxygen atoms present are those in ether groups, in ester groups, in the carbonyl groups of ketones, or in the hydroxyl groups of alcohols. The oxygenated hydrocarbon used as the solvent must be free of ethylenic and acetylenic unsaturation, although aromatic compounds—which are sometimes referred to as having aromatic unsaturation—are acceptable but not preferred. Preferably the oxygenated hydrocarbon is one which contains from 3 to 12 carbon atoms and contains no more than 3 oxygen atoms.

In addition, the solvent must be relatively non-polar, that is have a dielectric constant less than that of methanol, so that the solvent does not interfere with the methanol present; and it must be a weakly coordinating solvent such that it does not coordinate strongly with the cobalt catalyst. The solvent must be substantially inert under reaction conditions, that is it should not under the reaction conditions react to any appreciable extent either with itself or with the reactants, catalyst and reaction products present in the reaction mixture. This is not to say that the solvent must not react at all since a small amount of some of the solvents, particularly the alcohols, may undergo reaction and be converted to other products. The solvent must also be one which has a normal boiling point (that is, at atmospheric pressure) of at least 65° C. and which is a liquid at 35° C. and atmospheric pressure. Preferably the solvent will have a boiling point greater than the ethanol and the other oxygenated hydrocarbon reaction products in order to facilitate separation and recovery of the solvent by distillation; and, therefore, it is preferred that the solvent be one which has a normal boiling point of at least 80° C. and which is a liquid at 35° C. and atmospheric pressure.

The esters which may be used as solvents in the present invention may be aromatic or non-aromatic, and may contain one or a plurality of ester groups. Preferably the ester is an acyclic monoester. Suitable esters include methyl benzoate, butyl acetate, isopropyl isobutyrate, propyl propionate, dimethyl adipate.

Specifically as to alcohols, the alcohol utilized as a solvent is preferably a monohydric alcohol, that is one which contains only one hydroxyl group, and is preferably non-aromatic. Preferably the alcohol is either a non-aromatic, monocyclic alcohol (a cycloalkanol) or an acyclic alcohol (an alkanol). Alcohols suitable as a solvent include cyclohexanol, 1-hexanol, 2-hexanol, neopentanol, 1-pentanol, 2-octanol and 2-methyl-2-octanol.

Ketones useful as solvents may be either cyclic or acyclic and are preferably non-aromatic. Cyclic ketones are preferably monocyclic. Suitable ketones include cyclohexanone, 2-methyl-cyclohexanone, cycloheptanone, 2-pentanone, 3-pentanone, butanone and acetophenone. The ketone is preferably one containing only a single oxygen atom in a single carbonyl group.

The ethers which may be utilized as solvents are preferably non-aromatic ethers free of oxygen atoms other than etheral oxygen atoms. They may be cyclic or acyclic, with heterocyclic ethers being preferred. Suitable ethers include 1,4-dioxane, 1,3-dioxane, isopropyl propyl ether, diethylene glycol dibutyl ether, dibutyl ether, ethyl pentyl ether, diphenyl ether, hexyl phenyl ether, anisole and tetrahydropyran.

The oxygenated hydrocarbons that may be used as solvents in the present invention may contain more than one type of oxygen group. For example, the oxygenated hydrocarbon may contain both a ketone carbonyl group and a ether group, both an hydroxyl group and an ether group, both an ester group and an hydroxyl group, or the like. Suitable oxygenated hydrocarbons which contain more than one type of functional oxygen-containing group include ethylene glycol-monoethyl ether, 2-methoxy-1-butanol, 5-hydroxy-2-hexanone, 4-methoxy-2-butanone, ethyl glycolate and 2-ethoxyethyl acetate.

Of all the solvents that may be utilized in the invention, the ethers, especially the monocyclic, heterocyclic ethers, are preferred. 1,4-Dioxane is the especially preferred solvent. The dialkyl ketones also give especially good results.

The present invention is applicable to those processes wherein the catalyst utilized is one consisting of cobalt carbonyl, not in conjunction with, or modified by, halides. The cobalt carbonyl catalyst may be added as a cobalt carbonyl, or may be formed in situ from a catalyst compound which will form cobalt carbonyl under reaction conditions. Cobalt acetate, cobalt oxide, cobalt napthenate and cobalt carbonate are examples of compounds which under reaction conditions will form a cobalt carbonyl. Dicobalt octacarbonyl or cobalt hydridocarbonyl is preferred as the source of the catalyst although tetracobalt dodecacarbonyl may also be the source. It is believed that cobalt hydridocarbonyl, $HCo(CO)_3$ or $HCo(CO)_4$, is the active form and that other cobalt carbonyls and the above mentioned cobalt compounds are converted to cobalt hydridocarbonyl under reaction conditions. The inventor does not, however, wish to be held to any particular theory or mechanistic disclosure.

The quantity of catalyst employed is not narrowly critical and can vary over a wide range. In general, the process is desirably conducted in the presence of a catalytically effective quantity of the catalyst, which gives a suitable and reasonable reaction rate. Generally, an amount of catalyst should be used which will provide from about 0.5 to 100 millimoles, from about 2 to 50 millimoles, of cobalt carbonyl calculated as dicobalt octacarbonyl, $Co_2(CO)_8$, per mole of methanol although higher amounts up to solubility limits of the catalyst may be used. The cobalt carbonyl will, up to certain limits, be soluble in the methanol and solvent, although the cobalt carbonyl precurser (such as cobalt oxide) may not be soluble.

The basic conditions for the reaction of the methanol with the synthesis gas are well known. Preferably the liquid, single phase methanol-solvent solution having the catalyst there is intimately contacted with the synthesis gas under reaction conditions, such as by bubbling the gas through the liquid. Although the cobalt carbonyl precurser may not be soluble in the methanol-solvent solution, solubilization will occur as cobalt carbonyl is formed under reaction conditions.

When the reaction is conducted in the absence of a solvent, only a single liquid phase occurs because the water and other liquid products formed in the reaction are soluble in, or miscible with, the methanol. Some of the solvents which may be used according to the present invention, may however result in there being two liquid phases in the reaction zone due to the large amount of water which is generated in the reaction. Thus if the water is immiscible with the solvent, such may result in an aqueous phase being formed. Where such an aqueous phase is formed, substantially all the oxygenated hydrocarbon products and any unreacted methanol, and some of the catalyst, will be contained in the aqueous phase, whereas the solvent and most of the catalyst will remain with the organic phase.

The operative temperature which may be employed can vary over a wide range of elevated temperatures. In general, the process can be conducted at a temperature within the range from about 150° to 250° C. with best results being obtained within the range of about 175° to 215° C. The process is suitably effected over a wide superatmospheric pressure range. The pressure utilized must be at least sufficient to maintain a liquid phase of the methanol and solvent at the reaction temperature involved and generally should not be below about 20 atmospheres absolute. Generally, a pressure within the range of about 20 to 700 atmospheres absolute should be used, although pressures within the range of about 130 to 400 atmospheres absolute are preferred.

The reaction should be allowed to proceed for a period of time sufficient to produce the desired ethanol product. In general, the residence time can vary from a few minutes to several hours although generally the residence time should be from about 0.5 to 10 hours, with times of from about 1 to 5 hours preferred. The proper residence time will of course vary according to such factors as temperature, pressure, catalyst concentration, and the like.

The composition of any particular synthesis gas will vary according to the source thereof although the composition or source is not particularly critical to the present invention. The relative amounts of carbon monoxide and hydrogen which are present in the gas to be reacted with the methanol can be varied over a wide range. Generally, an increase in hydrogen concentration will cause an increased selectivity to ethanol, but may cause a loss in reaction rate. Thus, a balance must be reached between selectivity and reaction rate. A typical synthesis gas will contain from about 30 to 60 mole percent of carbon monoxide and 40 to 70 mole percent of hydrogen, and such is a preferred mixture for the process. However, mixtures of hydrogen and carbon monoxide containing from 10 to 90 mole percent carbon monoxide and 90 to 10 mole percent hydrogen will also be satisfactory for practice of the invention. Some carbon monoxide must always be present since the catalyst will decompose in the absence of carbon monoxide.

The process can be executed in a batch, semi-continuous, or continuous fashion. It can be conducted in a single reaction zone or a plurality of reaction zones, in series or in parallel, or it may be conducted intermittently or continuously in an elongated tubular zone or series of such zones. The catalyst or catalyst precursor may be initially introduced into the reaction zone batchwise, or it may be continuously or intermittently introduced into such zone during the course of the reaction.

The ethanol, as well as other reaction products such as methyl acetate, acetaldehyde and dimethyl acetal and the solvent, can be recovered from the liquid product stream by several techniques well known in the art including fractional distillation, azeotropic distillation, etc., either directly from the liquid product or after extraction of the desired products into a suitable solvent. As pointed out above, with some solvents an aqueous fraction may result which is relatively easily separated by decantation or the like. The recovered unreacted methanol (if the process is operated at less than 100% methanol conversion) as well as some light ends such as dimethyl ether can advantageously be recycled back to the reaction as part of the methanol feed. In addition, methyl acetate and dimethyl acetal, if desired, can be hydrolyzed to acetic acid and methanol, or to acetaldehyde and methanol, with the recovered methanol being recycled as part of the methanol feed.

The cobalt catalyst can be recycled or recovered and converted to a convenient catalyst or catalyst precursor form before recycling by a number of techniques well known in the art. For example, after recovery of the desired products and unreacted methanol and removal of water from the liquid product stream, the remaining heavy ends, which contain the cobalt catalyst in a concentrated form, can be recycled directly to the reactor. Alternatively, the heavy ends plus cobalt catalyst can be passed through an ion-exchange resin to recover the cobalt, or a base added to precipitate the cobalt as a cobalt hydroxide, or a suitable solvent added to extract the cobalt from the heavy ends phase if the heavy ends are unsuitable for recycle. As stated before, the cobalt catalyst need not be recycled in the form of cobalt hydridocarbonyl or dicobalt octacarbonyl, but may be in the form of a precursor that will form the cobalt carbonyl catalyst under reaction conditions.

The solvent may also be recycled, with the point to which the solvent is recycled being dependent on the form in which it is recovered. Where a relatively high boiling solvent is used, a heavy ends fraction may be recovered which contains not only the solvent but also the cobalt catalyst. In this situation the heavy ends fraction may be recycled directly to the reactor. If the solvent is recovered as a separate stream, or recovered as a stream wherein it is mixed with methanol or the like, the recovered solvent may advantageously be recycled as part of the methanol feed.

As is usual in most processes involving recycling of materials, it will sometimes be necessary to purge a recycle stream in order to prevent build-ups of impurities. Many variations of the recovery schemes generally mentioned above will be apparent to those skilled in the art, and the present invention is not to be integrated as being limited to any particular recovery scheme.

The following examples are given in order to illustrate the present invention, but should not be interpreted as limiting the scope thereof. In the examples the molar efficiencies were calculated based on the total moles of liquid product recovered and on a product accounted for basis, and, water was not included as a product. Molar efficiency to a particular product "A" was calculated according to the formula:

$$\text{Molar efficiency} = \frac{\text{Moles product A recovered} \times 100\%}{\text{Moles all products recovered}}$$

Methanol conversion was calculated by determining the difference between moles of methanol fed and moles of methanol recovered, dividing such difference by the moles of methanol fed, and multiplying by 100%.

EXAMPLE 1

To a 300 milliliter stainless steel reactor capable of withstanding internal pressures of at least 400 atmospheres was charged 16.0 g of methanol, 48.0 g of 1,4-dioxane, and 3.4 g of dicobalt octacarbonyl. No source of halide moiety of any sort was present in the experiment of this example nor in any of the experiments of other examples which follow hereinbelow. The reactor was purged of air and pressured to about 213 atmospheres with synthesis gas composed of about 50 percent by volume carbon monoxide and 50 percent by volume hydrogen. The reactor was heated rapidly to about 180° C. while the reactants were continually agitated by rocking the reactor up and down. The pressure reached a maximum of about 310 atmospheres. Upon reaching the reaction temperature, the course of the reaction was followed by observing the decrease in pressure in the system. When the pressure had dropped to about 187 atmospheres (approximately 4 hours after reaching reaction temperature), the reaction was stopped. After cooling to ambient temperature the final pressure in the system was about 120 atmospheres and 77.2 g of liquid product was recovered. The liquid product was analyzed using standard gas chromatographic techniques. The analysis of the liquid product showed it to contain, by weight, 10.1 percent ethanol, 2.2 percent higher alcohols (normal propanol, isopropanol, normal butanol, and isobutanol), 1.5 percent acetaldehyde, 0.2 percent dimethylacetal, 0.5 percent methyl acetate, 0.3 percent ethyl acetate, 0.9 percent methyl formate, 10.3 percent water, 9.8 percent methanol, and 62.2 percent dioxane, the remainder being various minor amounts of oxygenated hydrocarbons. The molar efficiency for ethanol was calculated to be 69%, for methyl acetate 2.4%, and for acetaldehyde plus dimethylacetal 12%. Methanol conversion was 53%.

For comparison purposes, the same experiment is repeated using 64.0 g of methanol and 3.4 g of dicobalt octacarbonyl with no solvent. During the course of the reaction an additional 67 atmospheres of 50 percent by volume carbon monoxide and 50 percent by volume hydrogen is added. The molar efficiency to ethanol is only 51% with the molar efficiencies to methyl acetate and acetaldehyde plus dimethyl acetal now being 15% and 17%, respectively. Methanol conversion is about 34%.

EXAMPLE 2

The procedure of Example 1 is repeated except that the charge to the reactor consists of 48.0 g n-butanol, 16.0 g methanol, and 3.4 g of dicobalt octacarbonyl. The molar efficiency to ethanol is 65% with a methanol conversion of 30%.

EXAMPLE 3

The procedure of Example 1 is repeated except that the charge to the reactor consists of 48.0 g diethylene glycol dibutyl ether, 16.0 g methanol, and 3.4 g of dicobalt octacarbonyl. The molar efficiency to ethanol is 60% with a methanol conversion of 36%.

EXAMPLE 4

The procedure of Example 1 is repeated except that the charge to the reactor consists of 48.0 g cyclohexanol, 16.0 g methanol, and 3.4 g of dicobalt octacarbonyl. The molar efficiency is 65% with a methanol conversion of 60%.

EXAMPLE 5

The procedure of Example 1 is repeated except that the charge to the reactor consists of 48.0 g of 3-pentanone, 16.0 g methanol, and 3.4 g of dicobalt octacarbonyl. The molar efficiency to ethanol is 65% with a methanol conversion at 66%.

EXAMPLE 6

The procedure of Example 1 is repeated except that the charge to the reactor consists of 48.0 g cyclohexanone, 16.0 g methanol, and 3.4 g of dicobalt octacarbonyl. The molar efficiency to ethanol is 68% with a methanol conversion of 66%.

EXAMPLE 7

The procedure of Example 1 is repeated except that the charge to the reactor consists of 48.0 g neopentanol, 16.0 g methanol, and 3.4 g of dicobalt octacarbonyl. The molar efficiency to ethanol is 69% with a methanol conversion of 56%.

EXAMPLE 8

The procedure of Example 1 is repeated except that the charge to the reactor is 32 g methyl butyrate, 32 g methanol, and 3.4 g dicobalt octacarbonyl. The molar efficiency to ethanol is 63% with a methanol conversion of 50%.

The embodiments of the invention in which an exclusive right or privilege is claimed are defined as follows:

1. In a reaction process wherein methanol is reacted, in the liquid phase at elevated temperature and superatmospheric pressure and in the presence of a catalyst consisting of cobalt carbonyl, with a gas comprising carbon monoxide and hydrogen to produce a product comprising ethanol, the improvement which comprises:
   conducting the reaction in a liquid oxygenated hydrocarbon solvent in which methanol and cobalt carbonyl are soluble under reaction conditions, which has a dielectric constant less than that of methanol, which does not coordinate strongly with cobalt carbonyl, and in which the only oxygen atoms present are ethereal oxygen, oxygen of the hydroxyl group of an alcohol, oxygen of an ester group, or oxygen of a ketone group of a ketone, said oxygenated hydrocarbon being a member of the group consisting of 1,4-dioxane, cyclohexanol, 3-pentanone, cyclohexanone, n-butanol, diethylene glycol dibutyl ether, neopentanol, and methyl butyrate.

2. The improvement of claim 1 wherein said oxygenated hydrocarbon solvent is a member of the group consisting of 1.4-dioxane, cyclohexanol, 3-pentanone, and cyclohexanone.

3. The process of claim 2 wherein said oxygenated hydrocarbon is 1,4-dioxane.

* * * * *

UNITED STATES PATENT AND TRADEMARK OFFICE
CERTIFICATE OF CORRECTION

PATENT NO. : 4,168,391
DATED : September 18, 1979
INVENTOR(S) : William E. Slinkard, Anthony B. Baylis It is certified that error appears in the above-identified patent and that said Letters Patent are hereby corrected as shown below:

In column 6, line 2, for "integrated" read -- interpreted --.

Signed and Sealed this

Eighteenth Day of December 1979

[SEAL]

Attest:

SIDNEY A. DIAMOND

Attesting Officer

Commissioner of Patents and Trademarks